United States Patent [19]

Jones et al.

[11] 4,032,546

[45] June 28, 1977

[54] BIS(BENZIL) TYPE COMPOUNDS CONTAINING ONE OR TWO FURAN MOIETIES

[75] Inventors: Robert J. Jones, Hermosa Beach; Michael K. O'Rell, Manhattan Beach, both of Calif.

[73] Assignee: TRW Inc., Redondo Beach, Calif.

[22] Filed: May 12, 1975

[21] Appl. No.: 576,827

Related U.S. Application Data

[63] Continuation-in-part of Ser. No. 411,512, Oct. 31, 1973, abandoned.

[52] U.S. Cl. .......................... 260/347.2; 260/347.8
[51] Int. Cl.² ...................................... C07D 307/46
[58] Field of Search ...................... 260/347.8, 347.2

[56] References Cited

UNITED STATES PATENTS 3,580,925  5/1971  Manos ........................... 260/347.8

Primary Examiner—Henry R. Jiles
Assistant Examiner—Bernard Dentz

Attorney, Agent, or Firm—John J. Connors; Donald R. Nyhagen; Alan D. Akers

[57] ABSTRACT

A monomeric bis (benzil) composition is produced by reacting furfural with an aromatic dialdehyde, the product having the structure:

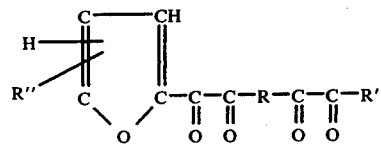

wherein R is a difunctional aromatic radical, R' is a hydrogen, a phenylene, or a furan radical, and R" is a hydrogen or or an alkyl substituent. These monomers are used to prepare cross-linked polyquinoxaline resins which have enhanced thermal and mechanical properties. Polymerization of these bis(benzil) monomers occurs by the reaction of the carbonyl groups with a tetraamine monomer. Cross-linking of the resulting polymers chains is accomplished by reaction of the furan end-cap group in a Diels-Alder reaction with a bis(dieneophile) substantially aromatic in composition.

1 Claim, No Drawings

BIS(BENZIL) TYPE COMPOUNDS CONTAINING ONE OR TWO FURAN MOIETIES

This application is a continuation-in-part of Ser. No. 411,512, filed Oct. 31, 1973 and now abandoned.

CROSS-REFERENCE TO RELATED APPLICATIONS

The bis(benzil) monomers disclosed herein are used in the polyquinoxalines disclosed in copending application entitled "Cross-linked Polyphenylquinoxaline Polymers," Ser. No. 411,511, filed Oct. 31, 1973 and now U.S. Pat. No. 3,904,584.

BACKGROUND OF THE INVENTION

Bisglyoxal monomers have been prepared by oxidation of diacetyl compounds which have been prepared by Friedel-Crafts acylation of the corresponding dicarboxylic acid chloride to the methyl ketone. These prior art bisglyoxals have had the general structural formula:

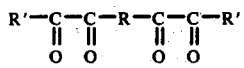

where R was a difunctional aromatic radical and R' was a phenylene radical, or more frequently, a hydrogen radical. The linear polyquinoxalines made from these bisglyoxals generally exhibited poorer thermal stability if the bisglyoxal was hydrogen terminated rather than aromatic terminated. However, the hydrogen terminated compound produced polymers which exhibited better adhesive qualities than the fully aromatic counterparts. In both instances, either the thermal or mechanical properties of the linear polymers were relatively poor.

SUMMARY OF THE INVENTION

The present invention relates to an end-capped bisglyoxal monomer produced by the reaction of furfural with an aromatic dialdehyde. The glyoxal monomer which is formed has two reactive furan groups which may be subsequently reacted with a bis(dieneophile) by a Diels-Alder reaction. The structure of the monomer may be illustrated as:

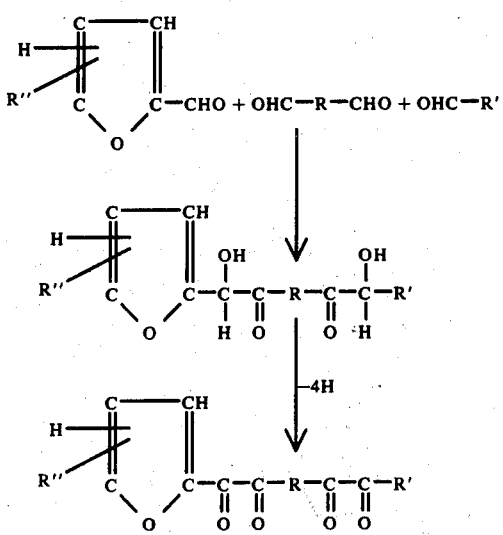

where R is a difunctional aromatic radical, R' is a hydrogen, an aromatic radical, or a furan radical, and R" is a hydrogen or an alkyl substituent. The end-capped glyoxal monomer may be used as a polymer constituent, in which case the carbonyl groups react with a tetraamine to produce a quinoxaline linkage, and it may be used as a cross-linking site by reacting a dieneophile with the furan end-cap. The bisglyoxal monomers of this invention provide a linear polymeric constituent which in turn will form an endooxy linkage upon reaction with an olefinic cross-linking agent to produce a polyphenylquinoxaline polymer of high thermal/mechanical integrity during fabrication steps, particularly when the polymer is cured subsequently by aromatizing the endooxy linkage to provide an insoluble aromatic polymer matrix. Further details of the polymer fabrication from these monomers may be found in the cross-referenced application which is incorporated herein by reference.

DESCRIPTION OF THE PREFERRED EMBODIMENTS

Bis(benzil) compounds according to the present invention are prepared by the reaction of 1 mole of an aromatic dialdehyde with 2 moles of another aldehyde, at least 1 mole of which is furfural. The compounds are reacted by refluxing with a cyanide catalyst to produce the corresponding bis-(hydroxycarbonyl) or benzoin compound. Subsequently, the bis-(hydroxycarbonyl) aromatic compound is oxidized to produce the corresponding bisglyoxal aromatic compound.

To produce the furan containing bisglyoxal of this invention, the furfural may be reacted with a wide variety of aromatic dialdehydes. Suitable dialdehydes may be represented by the following structure:

wherein R is a difunctional aromatic radical which may be selected from any of the following:

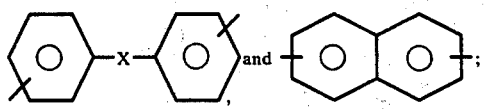

where X may be

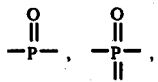

$-S-$, $-O-$, $-SO_2-$, $-CO-$,

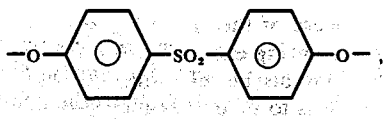

$-CH_2-$, $-C_2H_4-$, and $-C_3H_6-$.

The bis(benzil) monomers can be synthesized to have one or two furan ring end-caps. If two furan ring end-caps are desired, then the aromatic dialdehyde is reacted with furfural in a ratio of 1 mole of dialdehyde to 2 moles of furfural. However, if only one furan ring end-cap is desired, then the aromatic dialdehyde is reacted with only 1 mole of furfural and the other mole comprising another aldehyde; for example, formaldehyde, benzaldehyde, or tolualdehyde, which appears as R' below. A solution of the compounds is refluxed briefly in the presence of a cyanide catalyst. The reaction may be illustrated as follows:

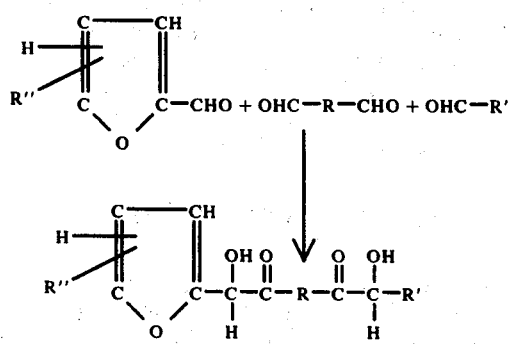

where R and R' have been defined previously, but R' usually consists of the following:

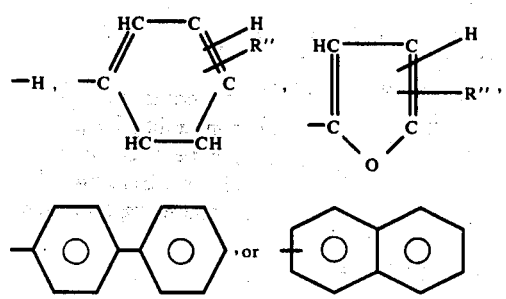

R" is an alkyl radical containing 1 to 4 carbon atoms.

The bis(hydroxycarbonyl) compound formed in the first reaction is subjected to an oxidizing reaction whereby the hydroxy substituents are oxidized to carbonyl, thus forming the bisglyoxal. The reaction may be illustrated:

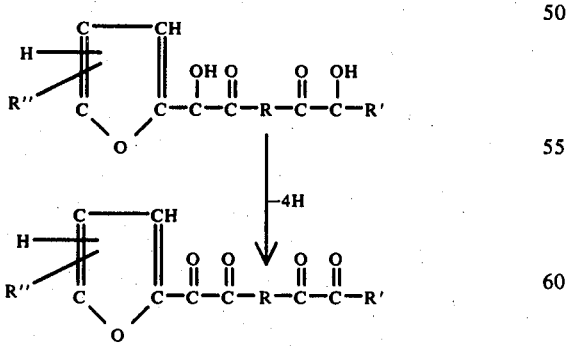

So that the process of this invention may be better understood, the following example teaches the method in preparation of the bis(benzil) monomers according to this invention. It is to be understood that the example is for the purpose of illustration and is representative of the many embodiments and combinations within the scope of this invention.

EXAMPLE I

Synthesis of 1,4-Bis(2-furylglyoxalyl) Benzene

To a mixture of 5.36 g (0.04 mole) of a terephthalaldehyde and 7.68 g (0.08 mole) of freshly distilled furfural in 80 ml of ethanol solvent was added a solution of 10.0 g (0.152 mole) of potassium cyanide in 40 ml of water. An exotherm occurred during the cyanide addition and a solid formed after 20 ml of the solution had been added. The reaction mixture was refluxed for 2 hours and then cooled to room temperature. A precipitate was collected by filtration and washed with ethanol. Recrystallized from a 50/50 v/v dimethylformamide/ethanol mixture gave 4.4 g (34%) of bis(hydroxycarbonyl) compound; m; 230°-233° C.

A well stirred mixture of 11.9 g (9.048 mole) of cupric sulfate pentahydrate in 6.0 ml of water and 14.0 ml of pyridine was heated until a solution was obtained. To this solution was added 4.0 g (0.012 mole) of the bis(hydroxycarbonyl) compound prepared above and the mixture was refluxed for 5 hours. After 20 minutes of refluxing, the initially blue solution had changed to green. The mixture was cooled to room temperature and then added to 500 ml of water. The precipitate was collected by filtration, washed well with water and recrystallized from ethanol. The fine yellow needles were collected by filtration and air dried to give 3.1 g.

The bis(benzil) compound prepared in this example is characterized by the following structure:

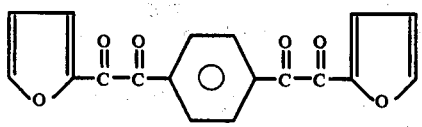

We claim:
1. A bis(benzil) compound of the formula:

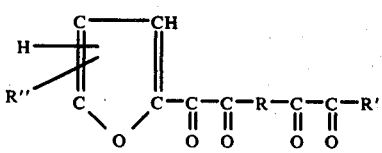

wherein R is a difunctional aromatic radical selected from the group consisting of

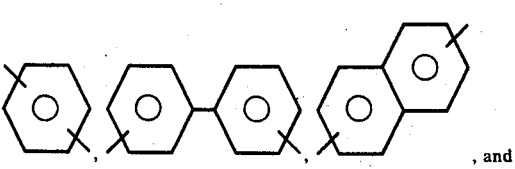

, and where X is —S—, —O—, —SO$_2$—, —CO—,

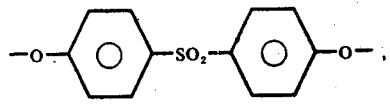
—CH$_2$—, —C$_2$H$_4$—, and —C$_3$H$_6$—; R' is a monofunctional radical selected from the group consisting of
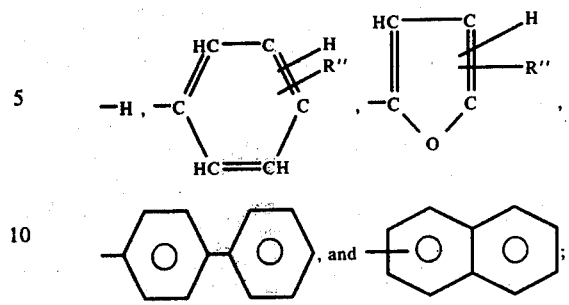
and R'' is a monofunctional radical which is selected from the group consisting of —H, —CH$_3$, —C$_2$H$_5$, —C$_3$H$_7$, and —C$_4$H$_9$.
* * * * *